(12) United States Patent
Keene et al.

(10) Patent No.: US 6,566,374 B1
(45) Date of Patent: May 20, 2003

(54) METHOD OF TREATING OR PREVENTING MICROBIAL INFECTIONS WITH LOPERAMIDE

(75) Inventors: Carol Keene, Shepperton (GB); Angus Malcolm, Cobham (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/601,300

(22) PCT Filed: Jan. 29, 1999

(86) PCT No.: PCT/EP99/00608
§ 371 (c)(1),
(2), (4) Date: Sep. 13, 2000

(87) PCT Pub. No.: WO99/39711
PCT Pub. Date: Aug. 12, 1999

(30) Foreign Application Priority Data

Feb. 5, 1998 (GB) ............................................... 9802542

(51) Int. Cl.[7] ..................... A61K 31/445; A61K 31/195
(52) U.S. Cl. ........................................ 514/315; 514/563
(58) Field of Search .................................. 514/315, 563

(56) References Cited

U.S. PATENT DOCUMENTS 5,994,372 A * 11/1999 Yaksh ........................ 514/327
6,156,771 A * 12/2000 Rubin et al. ................. 514/330

FOREIGN PATENT DOCUMENTS

DE            3906779 A1    3/1989
WO    PCT/EP99/00608    1/1999

OTHER PUBLICATIONS

Taraschewski, H. et al., "Loperamid, an efficacious drug against fishpathogenic acanthocephalus" *Parasitology Research*, vol. 76, No. 7, 1990, pp. 619–623.

Mehlhorn, H. et al. "Loperamid, an efficacious drug against the acanthocephalan macracanthorhynchus hirudinaceous in pigs" *Parasitology Research*, vol. 76, No. 7, 1990 pp. 624–626.

* cited by examiner

*Primary Examiner*—Kevin E. Weddington
(74) *Attorney, Agent, or Firm*—Nora Stein-Fernandez (57) ABSTRACT

A composition comprising loperamide or a pharmaceutically acceptable salt thereof for use in the prevention and/or treatment of microbial infections.

4 Claims, 6 Drawing Sheets

Figure 1:
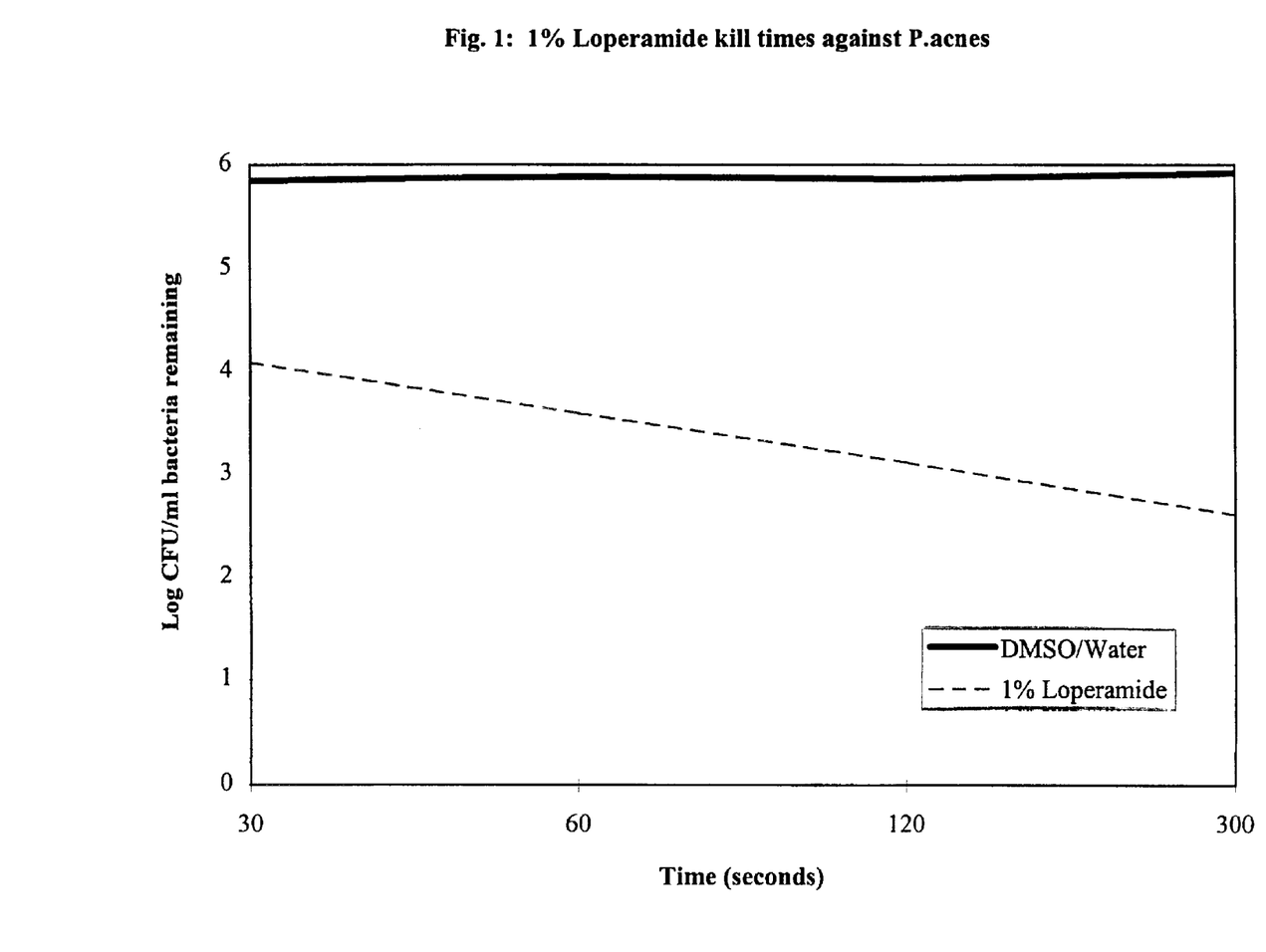

Fig. 1: 1% Loperamide kill times against P.acnes

Figure 2:
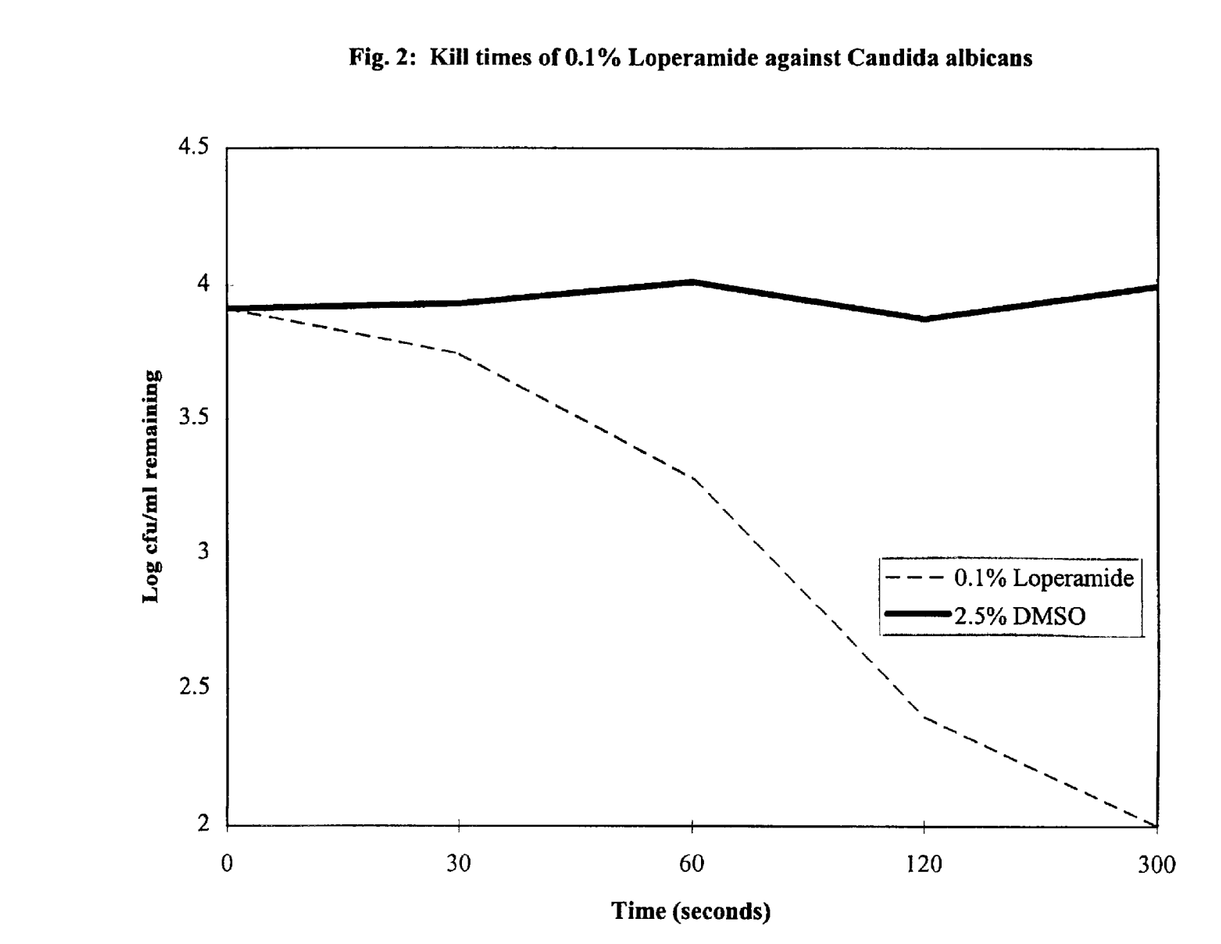

Fig. 2: Kill times of 0.1% Loperamide against Candida albicans

Figure 3:
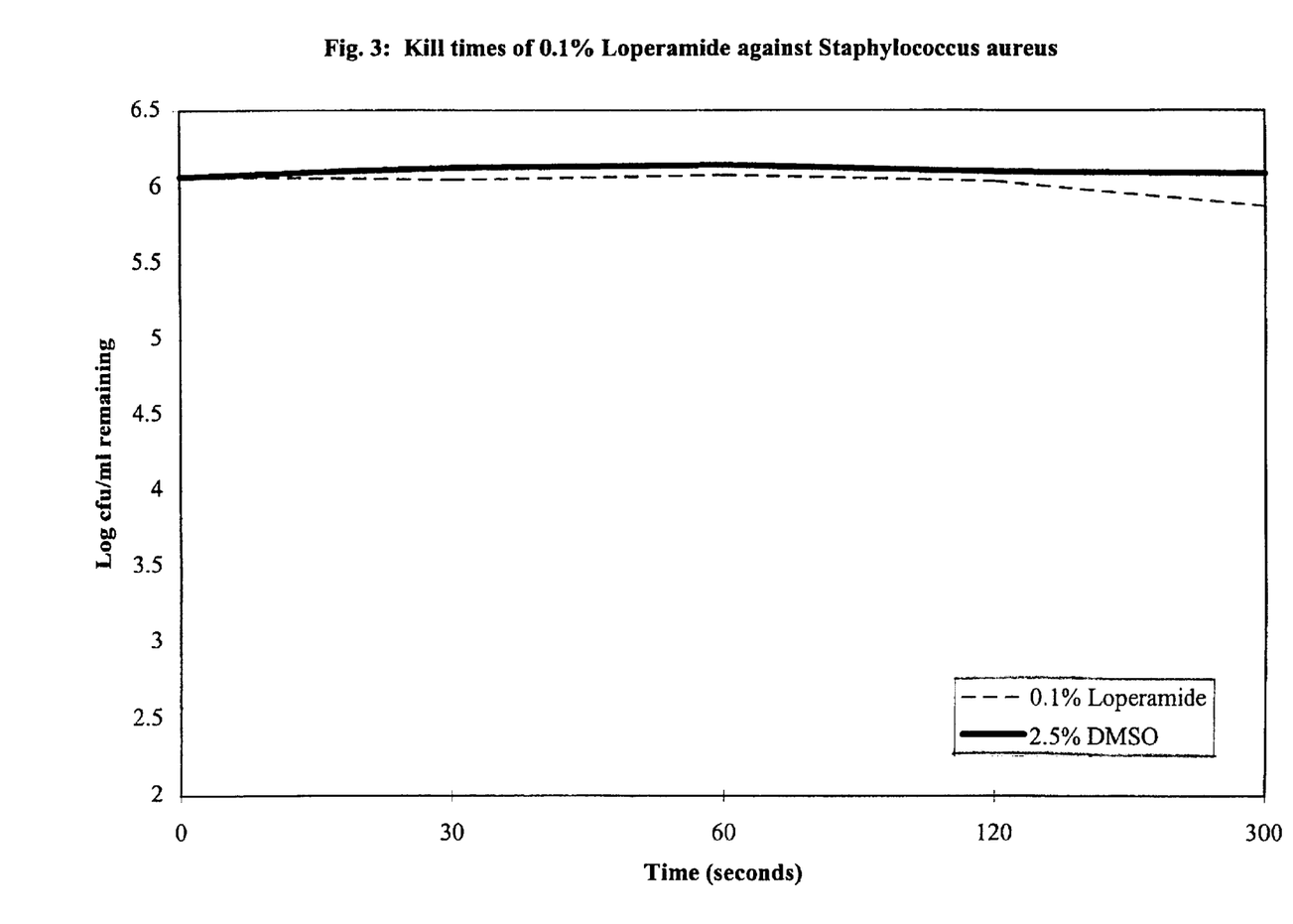

Fig. 3: Kill times of 0.1% Loperamide against Staphylococcus aureus

Figure 4:
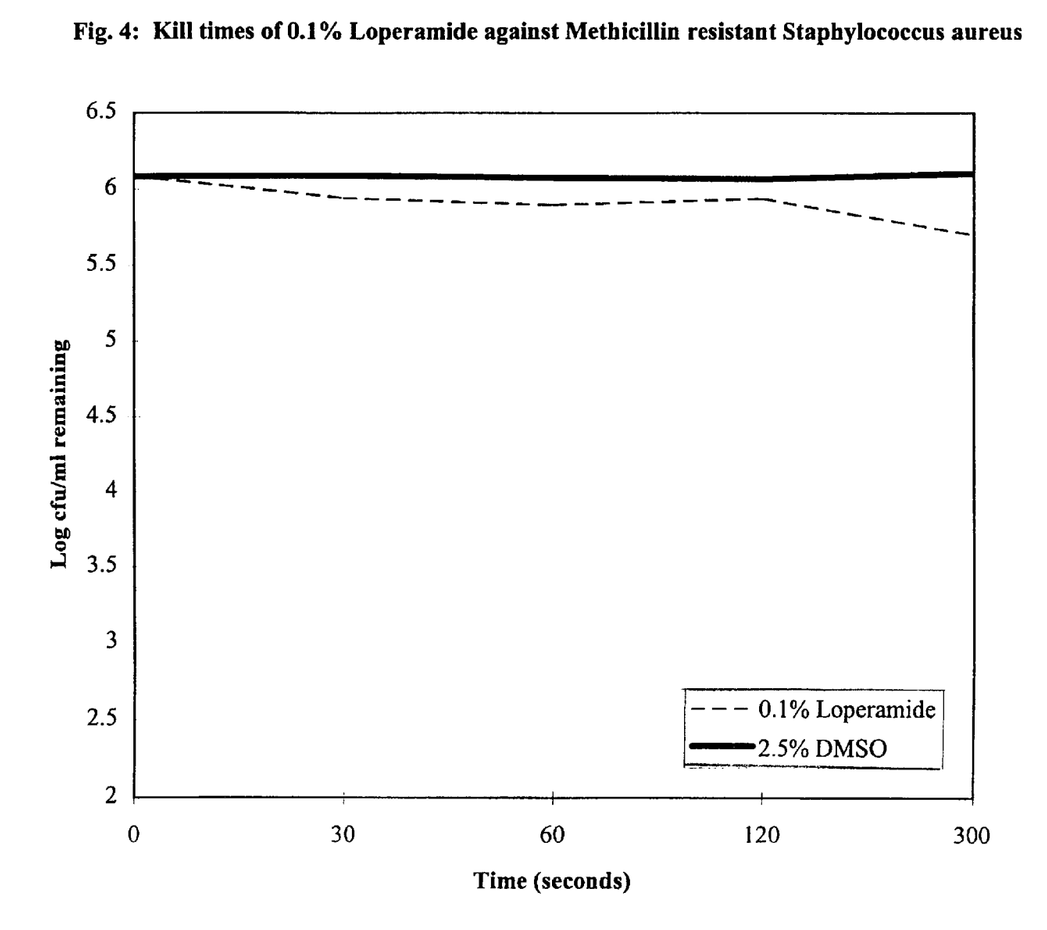
Figure 5:
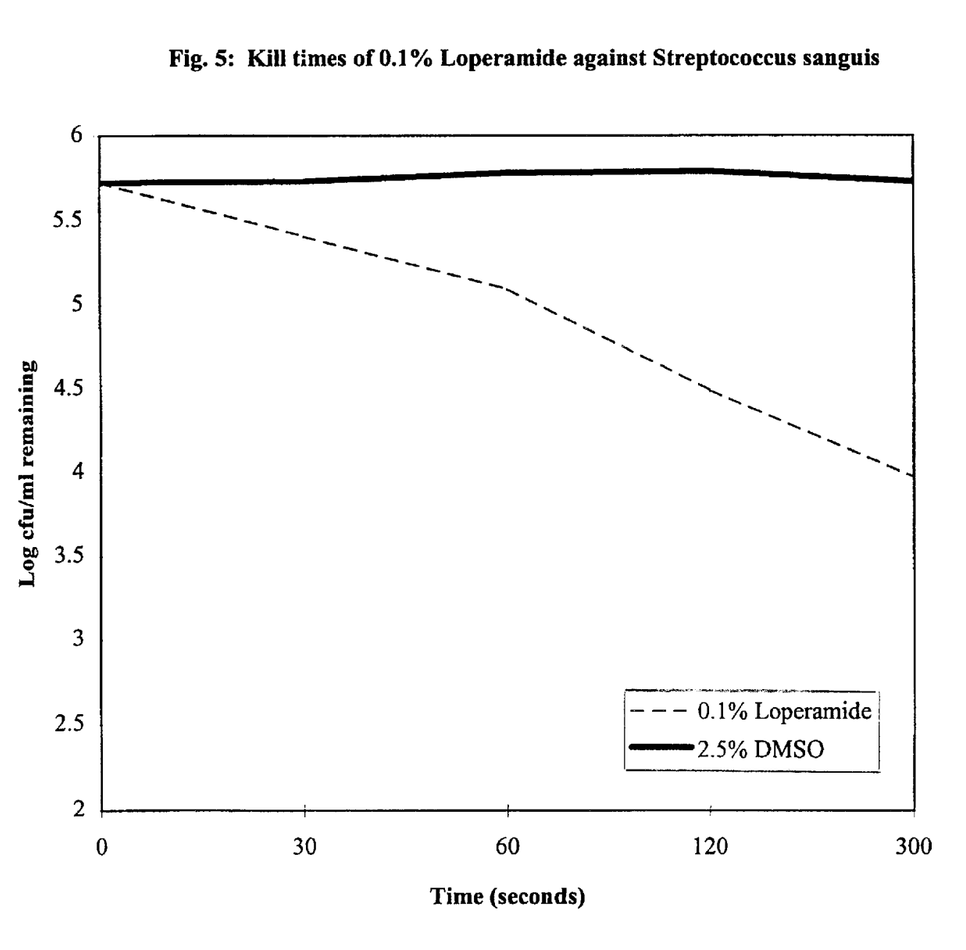
Figure 6:
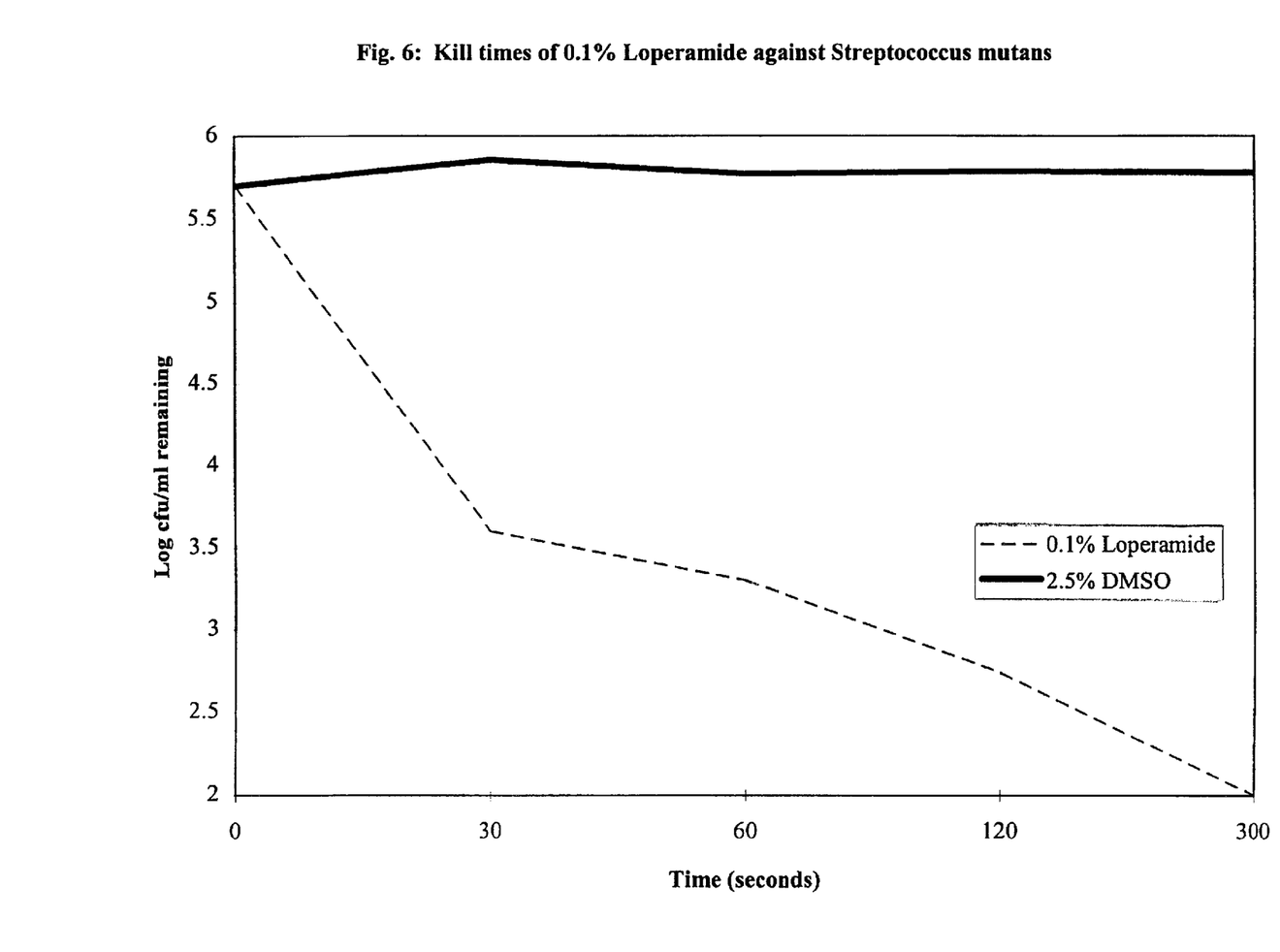

Fig. 4: Kill times of 0.1% Loperamide against Methicillin resistant Staphylococcus aureus Fig. 5: Kill times of 0.1% Loperamide against Streptococcus sanguis Fig. 6: Kill times of 0.1% Loperamide against Streptococcus mutans

METHOD OF TREATING OR PREVENTING MICROBIAL INFECTIONS WITH LOPERAMIDE

The present invention relates to the prevention and/or treatment of microbial infections and to the use of the compound, loperamide, in the preparation of a medicament for preventing and/or treating such infections.

Loperamide (4-(p-chlorophenyl)-4-hydroxy-N,N-dimethyl-α,α-diphenyl-1-piperidinebutyramide) is a synthetic opioid analogue. It is a selective opiate agonist drug which does not stimulate central nervous system opiate receptors. Loperamide has been used for many years as an orally administered treatment for acute and chronic diarrhoea (Merck Index, 12th Edition).

U.S. Pat. No. 5,116,847 discloses the use of loperamide and related compounds for the treatment of symptoms associated with respiratory diseases such as colds, flu, allergic and asomotor rhinitis, asthma, and bronchitis. Compositions for topical administration of these compounds to the eyes, nasal passages, sinuses, bronchial passages and the lungs are disclosed.

PCT publication, WO 95/27510, discloses the use of loperamide in the treatment of pathological conditions mediated by TNF (tumour necrosis factor). Skin inflammatory conditions are disclosed as being conditions mediated by TNF.

PCT publication, WO 97/09973, discloses the use of loperamide as an anti-hyperalgesic agent for the treatment or prevention of hyperalgesia. Compositions containing loperamide formulated for topical or local administration which exert anti-hyperalgesic activity via stimulation of peripheral opiate receptors are described.

Surprisingly, it has now been discovered that loperamide has antimicrobial activity. It has been shown to have activity against a wide range of microorganisms including anaerobes, fungi, Gram positive and Gram negative bacteria. Accordingly the present invention provides the use of loperamide or a pharmaceutically acceptable salt thereof in the manufacture of a medicament for use in the prevention and/or treatment of microbial infections.

Suitable pharmaceutically acceptable salts of loperamide include the hydrochloride, hydrobromide, acetate, citrate, lactate, tartrate, succinate and maleate salts. A preferred salt is the hydrochloride salt.

The present invention encompasses the use of loperamide or a pharmaceutically acceptable salt thereof as an antibacterial agent for the treatment of diseases and disorders of bacterial origin, e.g. in the treatment of boils, acne, atopic dermatitis, atopic eczema and psoriasis. Similarly, loperamide or its pharmaceutically acceptable salts may be used as an anti-antifungal agent for the treatment of diseases and disorders of fungal origin, e.g. in the treatment of yeast infections, such as cutaneous candidiasis or vaginal candidiasis, or to treat seborrhoeic dermatitis and other forms of dandruff. The present invention also extends to the use of loperamide or its pharmaceutically acceptable salts as a preservative to prevent microbial infection in a variety of healthcare or pharmaceutical compositions.

Compositions comprising loperamide and its pharmaceutically acceptable salts may be formulated for topical or oral administration. Accordingly the present invention provides a composition comprising an anti-microbial effective amount of loperamide or a pharmaceutically acceptable salt thereof and a carrier suitable for oral or topical administration, selected according to the particular type of presentation used.

Compositions comprising loperamide or a pharmaceutically acceptable salt thereof formulated for topical application include skin care compositions such as skin emollient, anti-dry scalp and anti nappy rash compositions; skin wash compositions such as soaps, skin washes, cleansers, anti-microbial hand washes and feminine care hygiene washes; shampoos such as anti-dandruff shampoos; antiperspirants; antibacterial treatments; and antifungal treatments, eg. compositions for the treatment of Candida (*Candida albicans*), tinea versicolor, ringworm, dandruff, athletes foot and jock-itch. A preferred antibacterial composition is an anti acne composition as defined herein below. Preferred antifungal compositions are anti-athlete's foot and anti-Candida compositions.

Compositions of the present invention comprising loperamide or its pharmaceutically acceptable salts formulated for oral administration include oral hygiene products, such as dental floss, and oral healthcare compositions such as toothpastes, abrasive and non-abrasive gels, mouthwashes, gargles, irrigating solutions, mouthsprays, and presentations for sucking or chewing by the user such as gums, pastilles and lozenges.

Antimicrobial applications for loperamide or its pharmaceutically acceptable salts also include compositions and products formulated for administration as suppositories or pessaries and in the form of vaginal tablets or implants. Yet further antimicrobial applications for loperamide or its salts include its use in spermicides and fungicides, in shoe inserts (odour eaters), and in sterilizers eg. for use in intravenous lines, catheter tips, contact lenses and bottles.

An amount of loperamide effective to treat microbial infections, eg. infections as hereinbefore described, depends on the nature and severity of the infection. Suitably the amount of loperamide or salt thereof in compositions for use in the present invention ranges from 0.0005 to 15%, preferably from 0.001 to 5%, even more preferably 0.01 to 1% by weight of the composition.

It will be appreciated by those skilled in the art that in order to ensure that the antimicrobial efficacy of loperamide or its salt thereof is preserved, compatible carrier and excipient components will be selected for inclusion in the compositions.

Suitable dermatologically-acceptable carriers for skin care and treatment products, for example for use in the treatment of acne or athlete's foot or Candida infections include gels, lotions, creams, ointments, solutions, sprays and the like. These are described in standard text books of pharmaceutics and cosmetics, such as Harry's Cosmeticology published by Leonard Hill Books, the British Pharmacopoeia, twenty first revision, (USP XXI)) (1984), distributed by the Mack Publishing Company. The carrier is generally organic in nature or is in the form of an aqueous emulsion and is capable of having the compound or salt thereof, which may be micronized, either dispersed, suspended or dissolved therein. The compositions usually comprise a unit dose of loperamide or salt thereof and contain conventional excipients well known in the art.

Gels for dermatological administration may comprise as components of the carrier a dermatologically acceptable solvent and a thickener. Suitable thickeners for use in the compositions of the invention include for instance, Carbomer eg Carbomer 934 manufactured by the BF Goodrich Company.

Creams may comprise an emulsifier, an oil phase ingredient and a solvent. Suitable emulsifiers include Cetomacrogol 1000 manufactured by ICI. Suitable oil phase ingredients include mineral oil eg. Crystosol USP 200 manufactured by the Witco Corporation.

Skin wash compositions may comprise an aqueous solvent and a detergent. A suitable detergent includes cocamidopropyl betaine eg. Tegobetaine F50, manufactured by Goldschmidt Ltd.

Oral hygiene compositions of the present invention may be provided in any of the presentations normally used for such products as hereinbefore defined. These compositions may be prepared as described in standard textbooks eg. Harry's Cosmeticology published by Leonard Hill Books, the British Pharmacopoeia, twenty first revision, (USP XXI) (1984), distributed by the Mack Publishing Company. Suitably such compositions may also usefully contain an ionic fluorine-containing compound such as fluoride salts e.g. amine fluorides and alkali metal fluoride salts, for example sodium fluoride, and monofluorophosphate salts such as alkali metal monofluorophosphate salts, for example sodium monofluorophosphate. Preferably the oral hygiene composition is in the form of a toothpaste composition which contains conventional excipients such as an abrasive, a thickening agent, as binding agent, surfactants and a humectant.

Suitable thickening and binding agents include xanthan gums, carrageenans, alginates, cellulose etherspolyoxyalkyl polymers and polyvinylpyrrolidone. Suitable humectarts include glycerin, propylene glycol, polyethylene glycol or mixtures thereof. Suitable surfactants include the water-soluble salts of alkyl sulphates having from 10 to 18 carbon atoms in the alkyl moiety, such as sodium lauryl sulphate, but other anionic surfactants as well as non-ionic, zwitterionic, cationic and amphoteric surfactants may also be used.

In addition, the compositions may optionally comprise sweetening agents, flavouring agents, anticaries agents, antiplaque agents, tooth desensitizing agents, colouring agents and pigments.

Oral hygiene compositions of the present invention in the form of liquid presentations, such as mouthwashes, gargles, or irrigating solutions, will preferably comprise as components of the carrier, a surfactant and an humectant as hereinbefore defined, in an aqueous or an aqueous ethanol solution.

The invention will now be illustrated by reference to the following examples.

EXAMPLE 1

Gel Formulation

|  | % w/w |
| --- | --- |
| Loperamide HCl | 5.0 |
| PEG-6 | 48.0 |
| Carbopol 980 | 0.3 |
| Triethanolamine | 0.5 |
| Deionised Water | to 100 |

EXAMPLE 2

Cream Formulation

|  | % w/w |
| --- | --- |
| Cetostearyl alcohol | 7.2 |
| Cetomacrogol 1000 | 1.8 |

-continued

|  | % w/w |
| --- | --- |
| White soft paraffin | 15.0 |
| Liquid Paraffin | 6.0 |
| PEG-6 | 30.0 |
| Loperamide HCl | 3.0 |
| Deionised Water | to 100 |

EXAMPLE 3

Skin Wash Formulation

|  | % w/w |
| --- | --- |
| Tegoglucoside L55 | 6.0 |
| Tegobetaine HS | 6.0 |
| Decyl Glucoside | 4.0 |
| Glucamate DOE 120 | 3.0 |
| Loperamide HCl | 1.0 |
| Deionised Water | to 100 |

EXAMPLE 4

Mouthwash

|  | % w/w |
| --- | --- |
| Ethanol | 20.00 |
| PEG 6 | 10.00 |
| Glycerin | 10.00 |
| Poloxamer | 1.00 |
| Flavour | 0.20 |
| Sodium Saccharin | 0.10 |
| Sodium Fluoride | 0.05 |
| FD&C Blue No. 1 | 0.001 |
| Loperamide | 1.00 |
| Purified water | to 100 |

EXAMPLE 5

Non-Alcoholic Mouthwash

|  | % w/w |
| --- | --- |
| PEG 6 | 15.00 |
| Glycerin | 15.00 |
| Sorbitol | 15.00 |
| Poloxamer | 2.00 |
| Ethoxylated (40) hydrogenated castor oil | 0.10 |
| Flavour | 0.20 |
| Sodium Saccharin | 0.10 |
| Sodium Fluoride | 0.05 |
| FD&C Blue No. 1 | 0.001 |
| Loperamide | 0.01 |
| Sodium Benzoate | 0.20 |
| Purified water | to 100 |

Determination of the Nominal Inhibitory Concentration of Loperamide

Method

A broth, appropriate to the microorganism to be tested (see Table 1 below), was inoculated aseptically from a pure plate culture and then incubated as indicated in Table 1.

Following the correct incubation, the liquid culture was diluted in a sterile saline solution to give approximately $10^5$ to $10^6$ CFU/ml. The suspension was serially diluted and spread plates were prepared for each dilution so as to obtain an accurate CFU/ml value.

The spiral plater was prepared by passing one cupule of IMS followed by one cupule of sterile water through the plater with the valve open and vacuum pump on. With the spiral plater cam on "Linear Deposition", the suspension of micoorganism to be tested was placed in a new cupule. The suspension was taken up, ensuring that the glass tube was full, and the organisms were then deposited in an even spiral onto agar plates.

The depth of the agar was measured on the plates and this value recorded. Negative control plates with no added active were produced in triplicate.

The spiral plater was washed with one cupule of IMS and one cupule of sterile deionised water in-between the inoculation of different microbial samples. Once the microbial inocula had dried, the spiral plater was washed and the cam changed to "Gradient Deposition". The antimicrobial solution was deposited in a spiral gradient directly on top of the dried inoculated spiral. Loperamide hydrochloride was used at concentrations of 1% and 0.3% made up in 50% dimethyl sulphoxide.

The spiral plater was washed with one cupule of IMS and one of sterile deionised water in-between different antimicrobial solutions. The solutions were left to dry before being incubated, at 37° C. for 24 hr, +/−6 hr or 48 hr +/−6 hr for anaerobes (see Table 1).

Following incubation, the control plates were checked to have grown to the end of the spiral inoculum. Digital calipers were used to measure the distance between the inoculation point and the point where confluent growth starts. The distance value termed the Radial Advance was used to determine the Deposition Factor (DF). The NIC can be calculated from the following formula:

NIC=(SC×DF)/ha where

NIC=Nominal Inhibitory Concentration (e.g. ppm)

SC=Stock concentration of antimicrobial (e.g. ppm)

DF=Deposition Factor ha=height of agar in plate (mm)

TABLE 1

| Microorganism | Inoculation Preparation Conditions | Test Plate Incubation Conditions |
| --- | --- | --- |
| P. acnes | 48 hrs BHI broth 37° C. anaerobically | 48 hrs BA 37° C. anaerobically |
| S. aureus | 24 hrs BHI broth | 24 hrs TSA 37° C. |
| S. epidermidis | 24 hrs BHI broth 37° C. | 24 hrs TSA 37° C. |
| M. luteus | 24 hrs TSB 37° C. | 24 hrs BA 37° C. |
| L. acidophillus | 24 hrs TSB 37° C. | 24 hrs BA 37° C. |
| C. albicans | 24 hrs TSB broth 37° C. | 24 hrs SDA 37° C. |
| S. sanguis | 24 hrs TSB broth 37° C. | 24 hrs BA 37° C. |
| S. mutans | 24 hrs TSB broth 37° C. | 24 hrs BA 37° C. |
| S. oralis | 24 hrs TSB 37° C. | 24 hrs BA 37° C. |
| F. nucleatum | 48 hrs BHI 37° C. (anaerobically) | 48 hrs BA 37° C. (anaerobically) |
| Ps. aeruginosa | 24 hrs TSB 37° C. | 24 hrs BA 37° C. |
| Ps. cepacia | 24 hrs TSB 37° C. | 24 hrs BA 37° C. |
| Ps. stutzeri | 24 hrs TSB 37° C. | 24 hrs BA 37° C. |
| S. paucimobilis | 24 hrs TSB 37° C. | 24 hrs BA 37° C. |

TABLE 1-continued

| Microorganism | Inoculation Preparation Conditions | Test Plate Incubation Conditions |
| --- | --- | --- |
| E. coli | 24 hrs TSB 37° C. | 24 hrs BA 37° C. |
| B. subtilis | 24 hrs TSB 37° C. | 24 hrs BA 37° C. |

BS = Blood Agar
TSB = Tryptone Soya Broth
TSA = Tryptone Soya Agar

Results

The results are tabulated below, see Table 2

TABLE 2

| Organism | NIC (ppm) |
| --- | --- |
| Propionibacterium acnes NCTC 737 | 16 |
| Staphylococcus aureus ATCC 6538 | 34 |
| Staphylococcus epidermidis ATCC 8853 | 33 |
| Micrococcus luteus NCIB 8166 | 9 |
| Lactobacillus acidophillus NCTC 4505 | 18 |
| Candida albicans NCYC 1363 | 39 |
| Streptococcus sanguis NCTC 10904 | 27 |
| Streptococcus mutans NCTC 11061 | 30 |
| Streptococcus oralis NCTC 11427 | 24 |
| Fusobacterium nucleatum NCTC 10562 | 7 |
| Pseudomonas aeruginosa ATCC 9027 | >165 |
| Pseudomonas cepacia ATCC 25416 | 36 |
| Pseudomonas stutzeri NCTC 10475 | 21 |
| Sphingomonas paucimobilis NCTC 11030 | 11 |
| Escherichia coli NCTC 8545 | >165 |
| Bacillus subtilis ATCC 6633 | 9 |

Conclusions

These results indicate that loperamide demonstrates good antimicrobial activity against a wide variety of organisms. The NIC values obtained are of a comparable level to many commonly used antimicrobials.

Determination of Effective Kill Times of Antimicrobial Solutions of Loperamide

Method

A suitable broth culture of the test organism was prepared (see Table 3 below). Cultures were diluted (1:10) using a Ringer and Peptone solution. 30 ml volumes of loperamide made up in 2.5% dimethyl sulphoxide were prepared. The samples were then inoculated with 30 ml of the initial microorganism suspension, and at time intervals of 30 seconds, 1, 2 and 5 minutes, 1 ml of the sample was removed and added to 9 ml of Dey-Engley neutralizing broth. Two further serial dilutions were then prepared.

0.1 ml from the Dey-Engley broths and subsequent dilutions were spread plated and then incubated. See Table 3 below for the appropriate agar and incubation conditions.

TABLE 3

| Microorganism | Inoculum Preparation | Test Media |
| --- | --- | --- |
| S. mutans | 24 hr BHI broth 37° C. | BA 37° C. |
| S. sanguis | 24 hr BHI broth 37° C. | BA 37° C. |
| S. aureus | 24 hr BHI broth 37° C. | TSA 37° C. |
| C. albicans | 24 hr SDA broth 37° C. | SDA 37° C. |

TABLE 3-continued

| Microorganism | Inoculum Preparation | Test Media |
|---|---|---|
| Methicillin resistant *S. aureus* | 24 hr BHI broth 37° C. | TSA 37° C. |
| *P. acnes* | 48 hr BHI broth 37° C. (anaerobically) | BA 37° C. (anaerobically) |

Results

The results are illustrated graphically in FIGS. 1–6.

Conclusions

These results show that loperamide has good bactericidal properties against a wide variety of organisms.

What is claimed is:

1. A method of treating or preventing microbial infections associated with skin disorders comprising topically administering loperamide, or a pharmaceutically acceptable salt thereof, in a suitable carrier.

2. The method as claimed in claim 1, wherein the pharmaceutically acceptable salt is the hydrochloride salt.

3. The method as claimed in claim 1, wherein the carrier comprises 0.001 to 5% by weight of loperamide or a pharmaceutically acceptable salt thereof.

4. The method as claimed in claim 3, wherein the carrier comprises 0.01 to 1% by weight of loperamide or a pharmaceutically acceptable salt thereof.

* * * * *